United States Patent [19]
Jew et al.

[11] Patent Number: 6,071,898
[45] Date of Patent: Jun. 6, 2000

[54] ASIATIC ACID DERIVATIVES HAVING MODIFIED A-RING

[75] Inventors: Sang Sup Jew; Hyeung Geun Park; Hee Doo Kim, all of Seoul; Young Hoon Jung, Kyunggi-do; Young Choong Kim, Seoul; Hong Pyo Kim, Seoul; Mi Kyeong Lee, Seoul; Hee Sung Choi, Seoul; Eung Seok Lee, Seoul; Chi Hyoung Yoo, Pusan; Doo Yeon Lim, Seoul; Jeong Hoon Kim, Seoul; Hee Man Kim, Seoul; Sung Ki Seo, Pusan; Tae Gyu Nam, Chungchongbuk-do; Ducky Han, Seoul; Pil Jong Shim, Seoul; Ju Eun Jung, Seoul; Hee Young Beom, Seoul, all of Rep. of Korea

[73] Assignee: Dong Kook Pharmaceutical Co., Ltd., Rep. of Korea

[21] Appl. No.: 09/308,875

[22] PCT Filed: Nov. 27, 1997

[86] PCT No.: PCT/KR97/00240

§ 371 Date: May 25, 1999

§ 102(e) Date: May 25, 1999

[87] PCT Pub. No.: WO98/23575

PCT Pub. Date: Jun. 4, 1998

[30] Foreign Application Priority Data

Nov. 27, 1996 [KR] Rep. of Korea ............... 96-58174
Feb. 28, 1997 [KR] Rep. of Korea ............... 97-6656

[51] Int. Cl.⁷ ............... A61K 31/56; C07J 53/00
[52] U.S. Cl. ............... 514/169; 514/893; 552/510
[58] Field of Search ............... 552/510; 514/169, 514/893

[56] References Cited

FOREIGN PATENT DOCUMENTS

WO 96/17819   6/1996   WIPO .

OTHER PUBLICATIONS

Singh et al., A reinvestigation of the triterpenes of centella asiatica>' Phytochemistry, ol. 8, pp. 917–921, 1969.

Osman, A.M. et al., "Chemical studies on pentacyclic triterpenes," *Chem Abstr*, 79:9249d (1973).

*Primary Examiner*—Barbara Badio
*Attorney, Agent, or Firm*—Heslin & Rothenberg, P.C.

[57] ABSTRACT

Asiatic acid derivatives having a modified A-ring, as represented by formula 1 are disclosed.

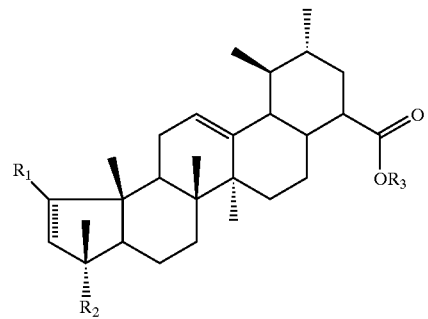

Pharmaceutical compositions and methods of treating cancer and hepatotoxicity utilizing compounds of formula 1 are also disclosed.

4 Claims, No Drawings

ASIATIC ACID DERIVATIVES HAVING MODIFIED A-RING

PRIOR FOREIGN APPLICATIONS

This application is a 371 of PCT/KR97/00240, filed Nov. 27, 1997 and claims priority from KR patent application numbers 1996/58174, filed Nov. 27, 1996 and 1997/6656, filed Feb. 28, 1997.

TECHNICAL FIELD

The present invention relates to asiatic acid derivatives having modified A-ring, which are represented by formula 1:

Formula 1

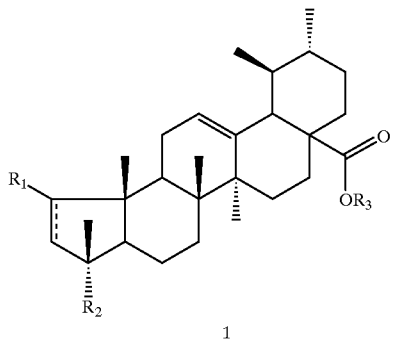

1 wherein, $R_1$ represents a lower alkyl group having 1–4 carbon atoms, an alkoxy group having 1–4 carbon atoms, hydroxymethyl group, a halomethyl group or an aldehyde group which may be protected by ethanedithiol; $R_2$ represents a lower alkyl group having 1–4 carbon atoms, t-butyldimethylsilyloxymethyl group, a halomethyl group, $-CH_2OCO(CH_2)_nCO_2H$ (n=0~3), $-CH_2OCOCHCHC_6H_5$, or hydroxy methyl group which may be protected by acetyl or benzoyl group; $R_3$ represents hydrogen or methyl group; and the double bond of 2-position may be reduced to form a single bond;

and anticancer agents and liver-function protecting agents containing the same as an active component.

BACKGROUND ARTS

These asiatic acid derivatives have been prepared by modifying A-ring of asiatic acid or methyl asiatate. The modification has been already performed to decide the structural formula of asiatic acid, and reported. [B. Singh and R. P. Rastogi, *Phytochemistry*, 8, 917–921, 1969]

Asiatic acid and asiaticoside (trisaccharide of asiatic acid) and madecassic acid, which are compounds extracted from *Centella asiatica*, were isolated firstly by Bontems in 1941 [J. E. Bontems, *Bull. Sci. Pharmacol.*, 49, 186–96 (1941)], and their structure was defined by Polonsky and his colleagues.[J. Polonsky, *Compt. Rend.*, 232, 1878–80 (1951): J. Polonsky, *Bull. Soc. Chim.*, 173–80 (1953)].

The extract including asiatic acid and asiaticoside from *Centella asiatica* have been used for treatment of hurted skin or chronic ulcer since old times, and also for treatment of skin deformation owing to tuberculosis or leprosy. [P. Boiteau, A. Buzas, E. Lederer and J. Polonsky, *Bull. Soc. Chim.*, 31, 46–51 (1949)]

Recently, it was reported that various triterpenes which have similar structure to asiatic acid extracted from plants, in particular, ursolic acid, show effect on cytotoxicity. [K. Yasukawa, *Oncology*, 48, 72–76 (1991); Dominic, Y. Alex, *Med. Sci. Res.*, 21(5), 213–215 (1993); Ryu, Shi young, *Arch. Pharamacal Res.*, 17(5), 375–7(1994)] It was reported that betulinic acid, which can be easily synthesized from its precursor isolated from the bark of white birch, shows cytotoxicity against melanoma cells without substantial side effect. [*Nat. Med.*, 1, 1046(1995)]

DISCLOSURE OF THE INVENTION

The present inventors have performed intensive studies to develop novel pharmaceutical compositions having various medical use, and as a result, they synthesized various derivatives having modified A-ring, starting from asiatic acid obtained from *Centella asiatica*. They also found that the derivatives have cytotoxicity and liver-protecting function and completed the invention.

The object of the present invention is to provide asiatic acid derivatives.

The present invention relates to asiatic acid derivatives represented by general formula 1:

Formula 1

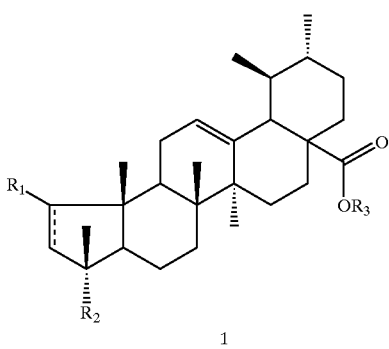

1 wherein, $R_1$ represents a lower alkyl group having 1–4 carbon atoms, an alkoxy group having 1–4 carbon atoms, hydroxymethyl group, a halomethyl group or an aldehyde group which may be protected by ethanedithiol; $R_2$ represents a lower alkyl group having 1–4 carbon atoms, t-butyldimethylsilyloxymethyl group, a halomethyl group, $-CH_2OCO(CH_2)_nCO_2H$ (n=0~3), $-CH_2OCOCHCHC_6H_5$, or hydroxy methyl group which may be protected by acetyl or benzoyl group; $R_3$ represents hydrogen or methyl group; and the double bond of 2-position may be reduced to form a single bond;

and anticancer agents and liver-function protecting agents containing the same as an active component.

The process for preparing the asiatic acid derivatives having modified A-ring according to the present invention is illustrated here-in-below:

Method 1

1) Asiatic acid (2) is treated with diazomethane to obtain methyl asiatate (3, $R_3$=methyl) quantatively, which is then oxidized to give a compound of lactol structure (4, $R_3$=methyl) in which A-ring have been modified. The compound is treated with catalytic amount of acetic acid/piperidine to obtain methyl A(1)-norursa-2,12-diene-23-hydroxy-2-formyl-28-oate (5, $R_3$=methyl). [See Scheme 1]

2) A compound having lactol structure (4, $R_3$=H) is obtained by using asiatic acid (2) as above, and the resultant compound is treated with acetic acid/piperidine catalyst to prepare A(1)-norursa-2,12-diene-23-hydroxy-2-formyl-28- carboxylic acid (5, $R_3$=H), which has modified A-ring. (See Scheme 1.)

Scheme 1

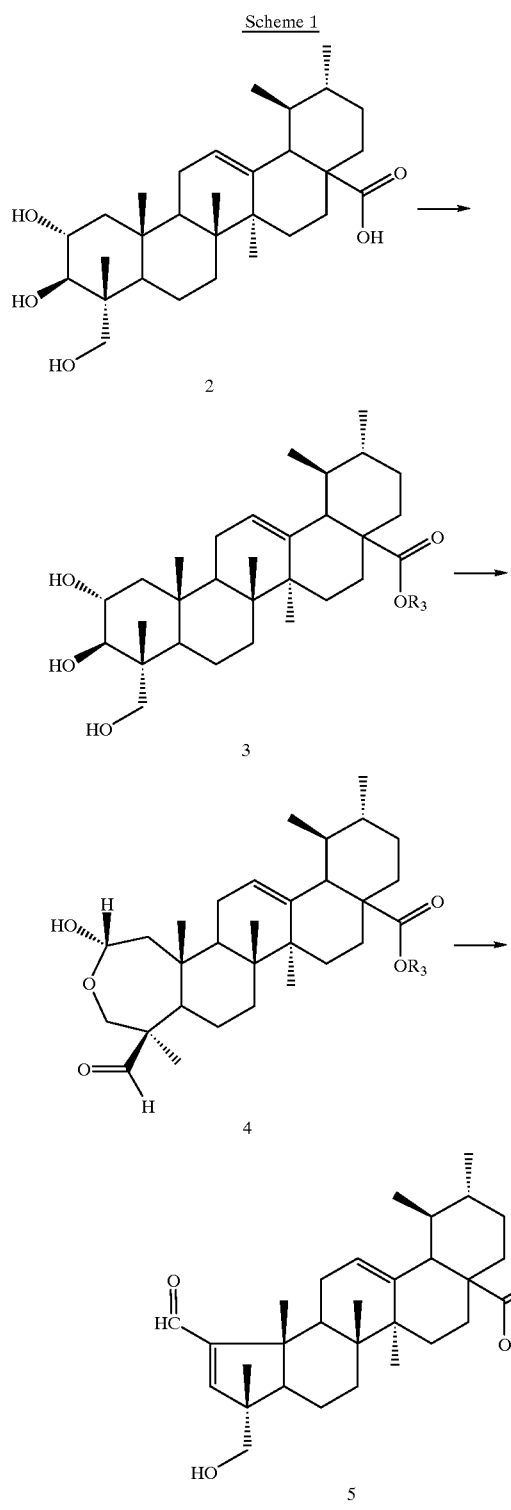

Method 2

A compound represented by general formula (6) is prepared by esterifying compound (5) obtained above with $R_4$COOH in the presence of catalyst. (See Scheme 2.)

Scheme 2

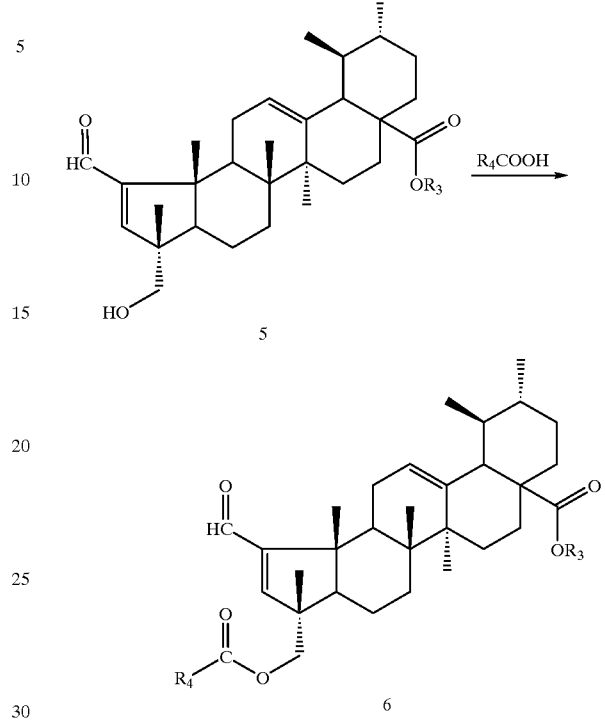

[In the formula, $R_4$ represents $(CH_2)_nCO_2H$, n=0~3, $CHCHC_6H_5$ or $C_6H_5$.]

Method 3

The compound (5) obtained above is treated with t-butyldimethylsilyl chloride and imidazole to obtain an intermediate of general formula (7), an intermediate of which 23-OH group has been protected. The aldehyde group of the resultant compound is reduced to obtain general formula (8), which is then halogenated to give an intermediate of general formula (9).

The intermediate compound of general formula (9) is treated with reducing agent and heated under reflux to obtain the compound of general formula (10), of which silyl group is then removed by using tetrabutylammonium fluoride to give the compound of general formula (11), a novel compound according to the present invention. (See Scheme 3.)

Scheme 3

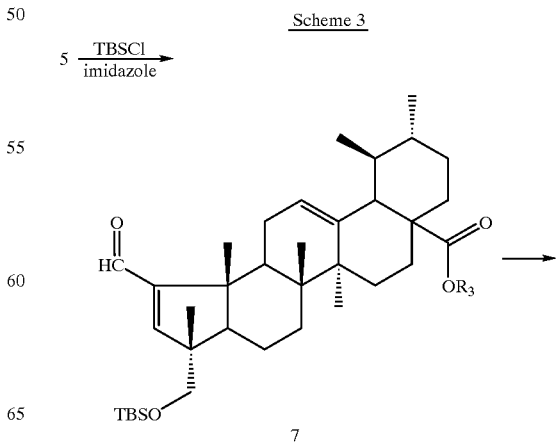

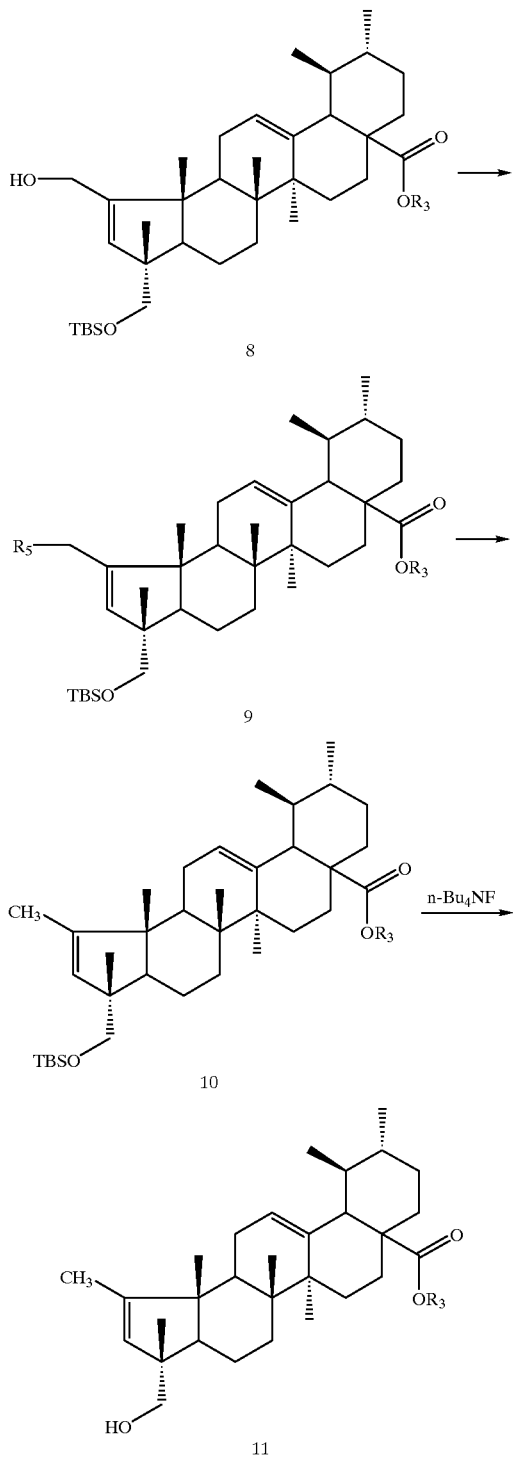

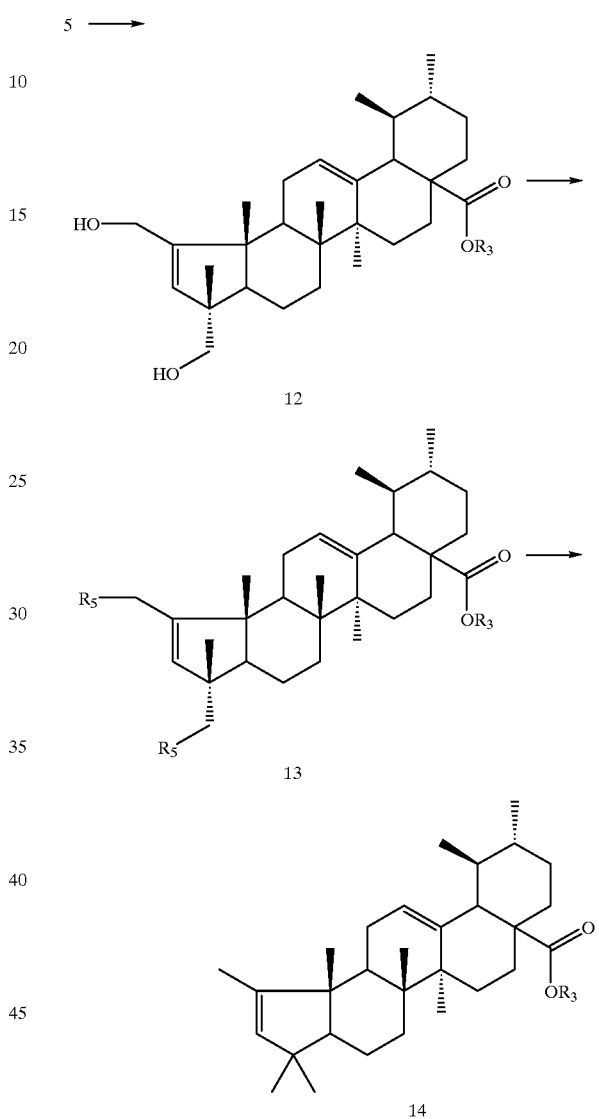

Method 4

The aldehyde group of compound (5) obtained above is reduced to obtain the compound of general formula (12), a novel compound according to the present invention, which is then treated with halogenating agent to give the compound of general formula (13).

Compound of general formula (13) obtained above is treated with reducing agent and heated under reflux to give the compound of general formula (14), a novel compound according to the present invention. (See Scheme 4)

Method 5

23-Hydroxy(OH) group of the compound of general formula(5) obtained above is acetylated to give a protected compound, the compound of general formula (15), which is then treated with diethylamine sulfur trifluoride to obtain the compound of general formula (16), a novel compound according to the present invention.

Compound of general formula (15) obtained above is reduced to give the compound of general formula (17), which is then treated with diethylamine sulfur trifluoride to obtain the compound of general formula (18), a novel compound. (See Scheme 5.)

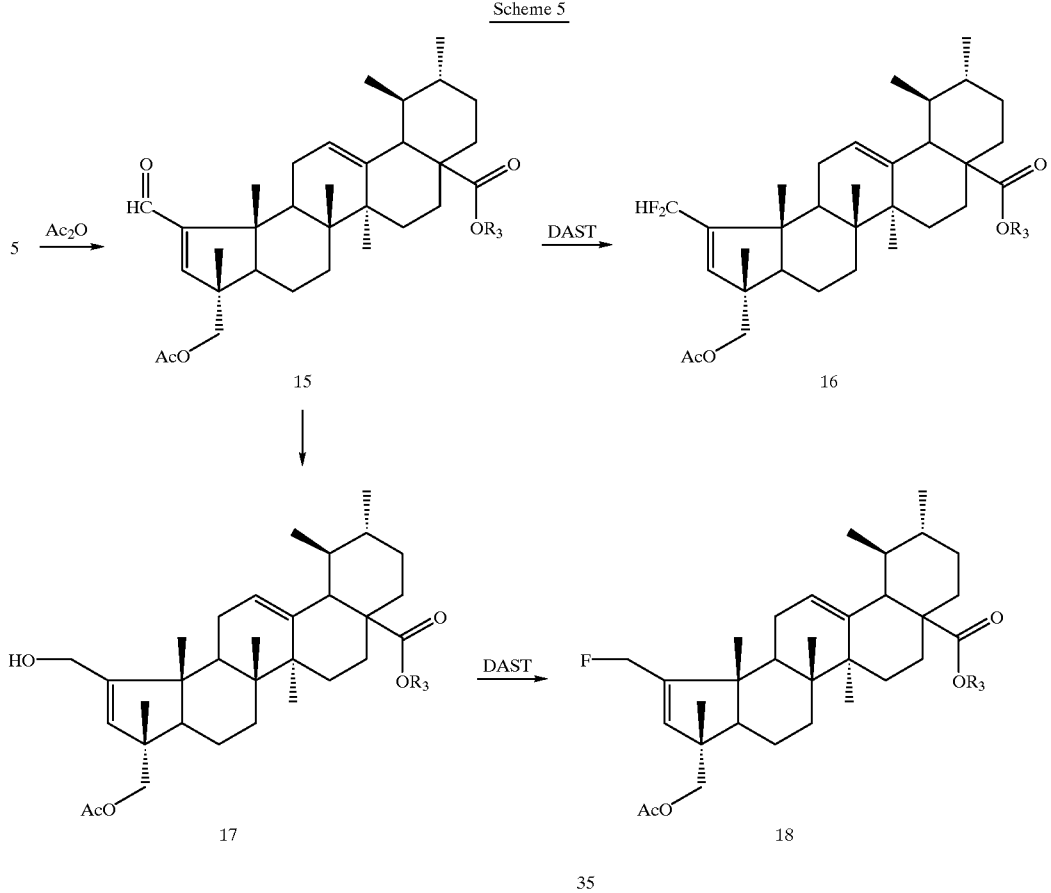

Scheme 5

Method 6

Compound of general formula (12) obtained above is reduced to give the compound of general formula (19), a novel compound. (See Scheme 6.)

Scheme 6

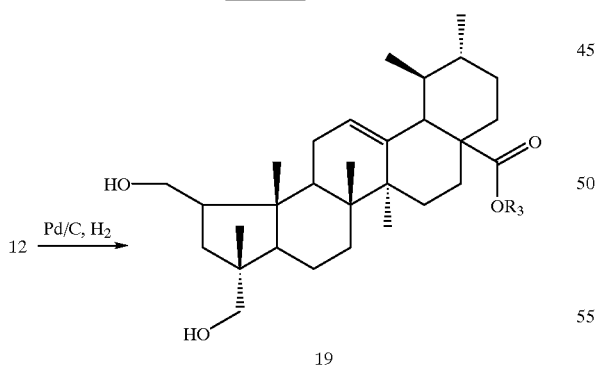

Method 7

Compound of general formula (5) obtained above is treated with ethanedithiol to obtain compound (20), which is protected by thioacetal. The general compound (20) is reduced with Raney Nickel to give the compound of general formula (21), a novel compound according to the present invention. (See Scheme 7.)

Scheme 7

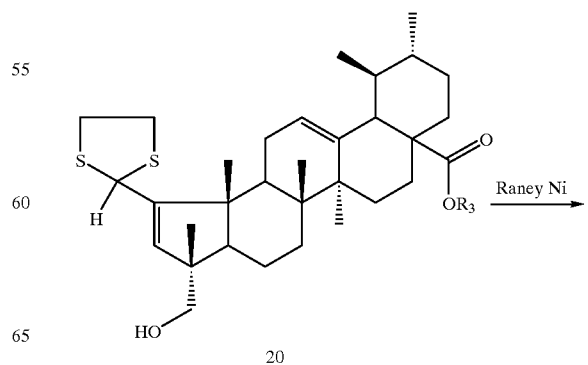

-continued

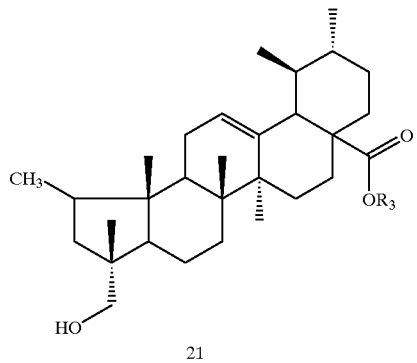

21

Method 8

Hydroxy group of compound of general formula (8) obtained above is methylated to give the compound of general formula (22), of which silyl group is then removed by using tetrabutylammonium fluoride to obtain the compound of general formula (23). (See Scheme 8.)

Scheme 8

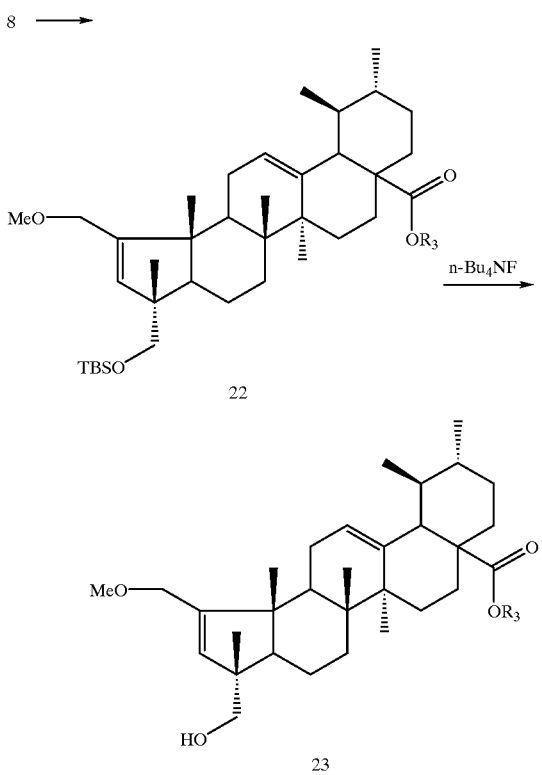

The dose of compound of general formula (1) is 0.01 to 1000 mg/day as anticancer agent, and 0.05 to 50 mg/day as a liver-protecting agent for an adult. The dose usually depends on age and body weight of a patient, as well as the condition of symptoms.

The anticancer agent and liver-protecting agent according to the present invention may be formulated into a suitable formulation for oral or parenteral administration by using conventional methods. For oral administration, it may be formulated as tablets, capsules, solution, syrup or suspension, while for parenteral administration, as transdermal or hypodermic injections, or injections into abdominal cavity or muscles.

BEST MODE FOR CARRYING OUT THE INVENTION

Now, the present invention is described with reference to Examples, Experimental Examples and Formulation Examples. However, it should be noted that the present invention is not restricted to those examples.

EXAMPLE 1

Preparation of methyl asiatate (3)

Asiatic acid (500 mg) was dissolved in methanol (25 ml), and the solution was cooled to 0° C. An excess amount of diazomethane/ether solution was added, and the resultant mixture was stirred at room temperature for 1 hour. The solvent was removed by evaporation under reduced pressure, and the residue was purified by column chromatography (eluent: dichloromethane/methanol=30:1) to give 490 mg of white solid(yield: 95%). The product was recrystallized from ethyl acetate to obtain needle-like crystals.

IR (neat): 3400, 1718 cm$^{-1}$; Mass (EI): m/e 503 (M$^+$+1), 467, 443, 262, 203, 189, 133; $^1$H-NMR(CDCl$_3$): δ 0.75, 0.91, 1.04, 1.08(each 3H, s), 0.85(3H,d,J=6.4 Hz), 0.94(1H, d,J=6.0 Hz), 2.23(1H,d,J=10.8 Hz), 3.41, 3.47(2H,ABq,J= 9.2 Hz), 3.60(3H,s), 3.69(1H,d,J=10.4 Hz), 3.73–3.80(1H, m), 5.25(1H,brt).

EXAMPLE 2

Preparation of Compound (4, R$_3$=methyl)

Methyl asiatate(1000 mg, 1.99 mmol) was dissolved in methanol:water=20:1, and NaIO$_4$ (645.6 mg) was added, and the resultant mixture was stirred at room temperature for about 3 hours. The solvent was removed by concentration under reduced pressure, and the residue was diluted with ethyl acetate, washed and dried. After filtration, the filtrate was concentrated under reduced pressure to give the residue, which was separated by column chromatography (dichloromethane:methanol=50:1) to give 790 mg of white solid (yield:79.3%).

IR(neat): 3426, 1713 cm$^{-1}$; Mass (EI): m/e 500(M$^+$); $^1$H-NMR (400 MHz, CDCl$_3$): δ 9.95(s,1H), 5.30(t,1H,J=3.2 Hz), 5.14–5.10(m, 1H), 3.93, 3.75(ABq,2H,J=13.6 Hz), 3.61(s,3H), 2.34(d,1H,J=2.9 Hz), 1.08, 1.06,1.00, 0.84(each s,3H), 0.85(d,3H,J=7.8 Hz).

Preparation of Compound(4, R$_3$=H)

Excepting from substituting asiatic acid for methyl asiatate, the same procedure as example 2 was used (yield:72.8%).

IR(neat): 3368, 2927, 1694 cm$^{-1}$; Mass (EI): m/e 486 (M$^+$); $^1$H-NMR (300 MHz, CDCl$_3$): δ 9.93(s,1H), 5.28(t, 1H), 5.10(m,1H), 3.91, 3.73(ABq, 2H, J=13.3 Hz), 2.19(d, 1H, J=10.5 Hz), 1.07, 1.04, 0.98, 0.82(each s, 3H), 0.93(d, 3H, J=5.61 Hz), 0.85(d, 3H, J=3.66 Hz).

EXAMPLE 3

Preparation of methyl A(1)-norursa-2,12-diene-23-hydroxy-2-formyl-28-oate(5, R$_3$=methyl)

Compound(4, 830 mg, 1.66 ml)was dried under reduced pressure and replaced with nitrogen and dissolved in anhydrous benzene. Acetic acid(20 ml), piperidine(20 ml) was added. The resultant solution was heat-refluxed at 60° C. for about 1 hour. After 1 hour anhydrous magnesium sulfate was added and heat-refluxed for 5 hours, the solvent was removed by evaporation under reduced pressure and the residue was diluted with ethyl acetate, washed and dried. The filtrate was concentrated under reduced pressure and purified separately by column chromatography (dichloromethane:methanol=80:1) to give 580 mg (yield:72.5%).

IR(neat): 3443, 1718, 1685 cm$^{-1}$; Mass (EI): m/e 483 (M$^+$+1); $^1$H-NMR (300 MHz, CDCl$_3$): δ 9.70(s,1H), 6.64 (t,1H), 5.26(t,1H,J=4.0 Hz), 3.59(s,3H), 3.54, 3.50(ABq, 2H, J=6.96 Hz), 1.23, 1.07, 1.01, 0.83(each s,3H), 0.91(d, 3H,J=5.61 Hz), 0.82(d,3H,J=6.36 Hz).

EXAMPLE 4

Preparation of methyl A(1)-norursa-2,12-diene-23-alkyl carbonyloxy-2-formyl-28-oate(6, R$_4$=—C$_2$H$_4$CO$_2$H)

Compound(5, 31.5 mg, 0.065 ml), succinic acid(8.49 ml), 1,3-dicyclohexylcarboimide(14.98 mg), 4-dimethylaminopyridine (0.80 mg) were dried under reduced pressure, the resultant was replaced with argon, dissolved in anhydrous dichloromethane and stirred at room temperature for 22 hours. The resultant was filtrated, and the filtrate was washed with dilute hydrochloric acid, water and saturated sodium chloride solution, and dried. The filtrate was dried under reduced pressure and purified separately by column chromatography(dichloromethane: methanol=20:1) to give 17.3 mg (yield:45.5%).

IR(neat): 2927, 1733 cm$^{-1}$; Mass (EI): m/e 582(M$^+$); $^1$H-NMR (300 MHz, CDCl$_3$): δ 9.69(s,1H), 6.56(s,1H), 5.28(s,1H), 5.26(t,1H), 4.06, 3.98(ABq, 2H, J=10.97 Hz), 3.59(s,3H), 2.65(s,4H), 1.23, 1.06, 1.03(each s,3H), 0.91(d, 3H, J=5.85 Hz), 0.83(d,3H, J=4.14 Hz).

Compound(6, R$_4$=—C$_3$H$_6$CO$_2$H)

Excepting from substituting glutaric acid for succinic acid, the same procedure as example 4 was used (yield:51.2%).

IR(neat): 2928, 1733 cm$^{-1}$; Mass (EI): m/e 596(M$^+$), 597, 598; $^1$H-NMR (300 MHz, CDCl$_3$): δ 9.69(s,1H), 6.58(s,1H), 5.26(t,1H), 4.05, 3.94(ABq,2H,J=10.7 Hz), 3.59(s,3H), 2.42 (t,2H,J=6.71 Hz), 2.21(d,1H,J=11.2 Hz), 1.95(t,2H,J=7.19 Hz), 1.22, 1.07, 1.05, 0.92, 0.82(each s,3H), 0.82(d,3H,J= 6.33 Hz).

Compound(6, R$_4$=—CHCHC$_6$H$_5$)

Excepting from substituting cinnamic acid for succinic acid, the same procedure as example 4 was used (yield:73.0%).

IR(neat): 2927, 1718 cm$^{-1}$; Mass (EI): m/e 612(M+), 613, 614; $^1$H-NMR (300 MHz, CDCl$_3$): δ 9.72(s,1H), 7.68(d,1H, J=15.8 Hz), 7.53–7.50(m,2H), 7.40–7.37(m,3H), 6.66(s, 1H), 6.43(d,1H,J=16.1 Hz), 5.27(t,1H), 4.17, 4.08(ABq,2H, J=10.95 Hz), 3.59(s,3H), 2.20(d,1H,J=10.5 Hz), 1.53, 1.24, 1.10; 1.04, 0.79(each s,3H), 0.90(d,3H,J=6.09 Hz), 0.82(d, 3H,J=5.13 Hz).

Compound(6, R$_4$=—C$_6$H$_5$)

Excepting from substituting benzoic acid for succinic acid, the same procedure as example 4 was used (yield:60.1%).

IR(neat): 2927, 1723 cm$^{-1}$; Mass (EI): m/e 586(M$^+$), 587; $^1$H-NMR (300 MHz, CDCl$_3$): δ 9.96(s,1H), 7.96(d,2H,J= 6.42 Hz), 7.51(t,1H,J=7.40 Hz), 7.38(t,2H,J=7.19 Hz), 6.63 (s,1H), 5.21(t,1H,J=3.53 Hz), 4.26, 4.11(ABq,2H,J=10.98 Hz), 3.54(s,3H), 2.15(d,1H,J=10.3 Hz) 1.20, 1.08, 0.95, 0.84, 0.76(each s,3H), 0.78(d,3H,J=2.19 Hz).

EXAMPLE 5

Preparation of methyl A(1)-norursa-2,12-diene-23-O-t-butyldimethylsilyl-2-formyl-28-oate(7)

Compound(5, 50 mg, 0.104 mmol) obtained above, imidazole(24.8 mg), t-butyldimethylsilylchloride(62.7 mg) were dried under reduced pressure and replaced with argon. The resultant mixture was dissolved in anhydrous dichloromethane, and stirred at room temperature for 6 hours. The solvent was removed by evaporation under reduced pressure. The residue was diluted with ethyl acetate, washed, to dried and filtrated. The filtrate was concentrated under reduced pressure and refined separately with column chromatography(hexane:ethyl acetate=10:1) to obtain transparent oily compound 56.2 mg. (yield:90.7%)

IR(neat): 1725, 1689 cm$^{-1}$; Mass (EI): m/e 596(M$^+$); $^1$H-NMR (400 MHz, CDCl$_3$): δ 9.70(s,1H), 6.63(s,1H), 5.29(t,1H,J=3.4 Hz), 3.61(s,3H), 3.52, 3.37(ABq,2H,J=9.5 Hz), 2.23(d,1H,J=10.7 Hz), 1.23, 1.08, 0.97, 0.84(each s,3H), 0.93(d,3H,J=5.9 Hz), 0.85(d,3H,J=6.4 Hz),0.88(s, 9H), 0.05(s,6H).

EXAMPLE 6

Preparation of methyl A(1)-norursa-2-hydroxymethyl-2,12-diene-23-O-t-butyldimethylsilyl-28-oate(8)

Compound(7, 91.7 mg, 0.154 mmol) obtained above, sodium borohydride(11.9 mg) were dried under reduced pressure and replaced with argon. The resultant mixture was dissolved in anhydrous methanol, and stirred at room temperature for 2 hours. The solvent was removed by evaporation under reduced pressure and refined separately with column chromatography(hexane:ethyl acetate=15:1) to obtain compound 91.4 mg (yield:99.3%).

IR(neat): 3449, 1724 cm$^{-1}$; Mass (EI): m/e 580(M$^+$–H$_2$O); $^1$H-NMR (400 MHz, CDCl$_3$): δ 5.40(s,1H), 5.23(t, 1H), 4.21, 4.12(ABq,2H,J=22.9 Hz), 3.60(s,3H), 3.38, 329 (ABq,2H,J=9.5 Hz), 2.22(d,1H,J=11.2 Hz), 1.15, 1.10, 0.93, 0.80(each s, 3H), 0.86(d,3H,J=6.4 Hz), 0.88(s,9H), 0.02(s, 6H).

EXAMPLE 7

Preparation of methyl A(1)-norursa-2-bromomethyl-2,12-diene-23-O-t-butyldimethylsilyl-28-oate(9, R$_5$=Br)

Compound(8, 54 mg, 0.090 mmol) obtained above, PPh$_3$ (35.8 mg), carbon tetrabromide(45.2 mg) were dried under reduced pressure and replaced with argon. The resultant mixture was dissolved in anhydrous dichloromethane, stirred at room temperature for 30 miniutes. The solvent was removed by evaporation under reduced pressure. The residue was diluted with ethyl acetate, washed, dried and filtrated. The filtrate was concentrated under reduced pressure, refined separately with column chromatography (hexane:ethyl acetate=10:1) to obtain compound 53.7 mg(yield:90%).

$^1$H-NMR (500 MHz, CDCl$_3$): δ 5.57(s,1H), 5.25(t,1H,J= 3.48 Hz), 4.08, 4.02(ABq,2H,J=11.1 Hz), 3.58(s,3H), 3.35, 3.26(ABq,2H,J=9.5 Hz), 2.20(d,1H,J=3.3 Hz), 1.10, 0.93, 0.81(each s,3H), 0.91(d,3H,J=4.05 Hz), 0.85(s,9H), 0.00(s, 6H).

EXAMPLE 8

Preparation of methyl A(1)-norursa-2-chloromethyl-2,12-diene-23-O-t-butyldimethylsilyl-28-oate(9, R$_5$=Cl)

Compound(8, 10.3 mg, 0.017 mmol) obtained above was dried under reduced pressure and replaced with argon. The resultant mixture was dissolved in anhydrous dichloromethane. Pyridine(1.38 μl) and SOCl$_2$(3.76 μl) were added to that at 0° C., stirred for 24 hours. Small amount of water was added and the solvent was removed by evaporation under reduced pressure. The residue was diluted with ethyl acetate, washed, and dried. The filtrate was concentrated under reduced pressure and refined separately with column chromatography (hexane:ethyl acetate=30:1) to obtain compound 0.6 mg yield:(5.7%).

IR(neat): 1726, 2928 cm$^{-1}$; $^1$H-NMR (400 MHz, CDCl$_3$): δ 5.56(s,1H), 5.25(t,1H,J=3.2 Hz), 4.17, 4.16(ABq,2H,J= 1.23 Hz), 3.61(s,3H), 3.38, 3.29(ABq,2H,J=9.27 Hz), 2.24 (d,1H,J=10.26 Hz), 1.19, 1.12, 0.94, 0.82(each s,3H), 0.95 (d,3H,J=5.37 Hz), 0.87(d,3H,J=7.81 Hz), 0.88(s,9H), 0.02 (s,6H).

EXAMPLE 9
Preparation of methyl A(1)-norursa-2-iodomethyl-2,12-diene-23-O-t-butyldimethylsilyl-28-oate(9, $R_5$=I)

Compound(8, 31 mg, 0.052 mmol) obtained above was dried under reduced pressure and replaced with argon. The resultant mixture was dissolved in anhydrous THF and stirred at 0° C. Methyltriphenoxyphosphonium iodide [$(PhO)_3P^+CH_3I^-$] which was dissolved in anhydrous THF was added to resultant solution and stirred for 30 minutes. 5% potassium carbonate was added to the resultant and the solvent was removed by evaporation under reduced pressure. The residue was diluted with ethyl acetate, washed, and dried. The filtrate was concentrated under reduced pressure, refined separately with column chromatography (hexane:ethyl acetate=10:1) to obtain compound.

$^1$H-NMR (500 MHz, $CDCl_3$): δ 5.57(s,1H), 5.26(t,1H), 4.06, 3.89(ABq,2H,J=10.25 Hz), 3.58(s,3H), 3.32, 3.24 (ABq,2H,J=9.48 Hz), 2.24(d,1H,J=10.26 Hz), 1.23, 1.18, 1.12, 0.81(each s,3H), 0.92(d,3H,J=6.4 Hz), 0.87(d,3H,J= 1.15 Hz), 0.87(s,9H), 0.01(s,6H).

EXAMPLE 10
Preparation of methyl A(1)-norursa-2-Methyl-2,12-diene-23-O-t-butyldimethylsilyl-28-oate(10)

Compound(9, 15.3 mg, 0.023 mmol) obtained above, sodium borohydride(1.79 mg) were dried under reduced pressure and replaced with argon. The resultant mixture was dissolved in anhydrous DMSO and stirred at room temperature for 4 hours. The solvent was removed by evaporation under reduced pressure and refined separately with column chromatography(hexane:ethyl acetate=30:1) to obtain compound 12 mg(yield:89%).

IR(neat): 2928, 1728 $cm^{-1}$; Mass (EI): m/e 582(M+); $^1$H-NMR (400 MHz, $CDCl_3$): δ 5.22(t,1H), 5.02(s,1H), 3.60(s,3H), 3.33, 3.24(ABq,2H,J=12.3 Hz), 2.21(d,1H,J= 15.4 Hz), 1.71(s,3H), 1.10, 1.08, 0.94, 0.79(each s,3H), 0.88(d,3H,J=9.4 Hz), 0.87(s,9H), 0.00(s,6H).

EXAMPLE 11
Preparation of methyl A(1)-norursa-2-methyl-2,12-diene-23-hydroxy-28-oate(11)

Compound(10, 12 mg, 0.021 mmol) obtained above was dried under reduced pressure and dissolved in anhydrous THF. Tetrabutylammoniumfluoride(6.0 mg) was added to the resultant mixture at room temperature and stirred for 24 hours. The solvent was removed by evaporation under reduced pressure and refined separately with column chromatography(hexane:ethyl acetate=10:1) to obtain compound 3.8 mg(yield:54.7%).

IR(neat): 3436 $cm^{-1}$; Mass (EI): m/e 469($M^+$+1); $^1$H-NMR (300 MHz, $CDCl_3$): δ 5.22(t,1H,J=3.29 Hz), 4.98 (s,1H), 3.59(s,3H), 3.37, 3.30(ABq,2H,J=8.04 Hz), 2.07(d, 1H,J=8.31 Hz), 1.75(s,3H), 1.10, 0.96, 0.88, 0.79(each s,3H), 0.84(d,3H,J=6.33 Hz).

EXAMPLE 12
The production of methyl A(1)-norursa-2-hydroxymethyl-2,12-diene-23-hydroxy-28-oate(12)

Excepting from substituting compound(5) for compound (7), the same procedure as example 6 was used (yield:89.9%).

IR(neat): 3368, 2926, 1733 $cm^{-1}$; Mass (EI): m/e 485 ($M^+$+1); $^1$H-NMR (400 MHz, $CDCl_3$): δ 5.40(s,1H), 5.23 (t,1H), 4.31, 4.22(ABq,2H,J=0.98 Hz), 3.61(s,3H), 3.47, 3.35(ABq,2H,J=10.7 Hz), 2.23(d,1H,J=11.2 Hz), 1.18, 1.12, 0.95, 0.81(each s,3H), 0.94(d,3H,J=6.3 Hz), 0.85(d,3H,J= 6.4 Hz).

EXAMPLE 13
Preparation of methyl A(1)-norursa-2-fluoromethyl-23-fluoro-2,12-diene-28-oate(13, $R_5$=F)

Compound(12, 25 mg,51.7 μmol) obtained above was dried under reduced pressure, replaced with argon and dissolved in anhydrous dichloromethane. Diethylaminosulfurtrifluoride(DAST, 20.5 μl) was added to resultant mixture at −78° C. and stirred at room temperatre for 1 hour and a half. Saturated sodium bicarbonate was added at 0° C. to resultant, washed and dried. The filtrate was concentrated under reduced pressure and refined separately with column chromatography (hexane:ethyl acetate= 15:1) to obtain compound 8.3 mg (yield:32.9%).

IR(neat): 2928, 1732 $cm^{-1}$; Mass (EI): m/e 488($M^+$).

EXAMPLE 14
Preparation of methyl A(1)-norursa-2-bromomethyl-23-bromo-2,12-diene-28-oate(13, $R_5$=Br)

Excepting from substituting compound(12) for compound (8), the same procedure as example 7 was used (yield:53.9%).

IR(neat): 2962 $cm^{-1}$; Mass (EI): m/e 610($M^+$); $^1$H-NMR (300 MHz, $CDCl_3$): δ 5.59(s,1H), 5.19(t,1H), 4.00, 3.99 (ABq,2H,J=1.71 Hz), 3.54(s,3H), 3.34, 3.22(ABq,2H,J=9.9 Hz), 1.19, 1.15, 1.06, 0.78(each s,3H), 0.87(d,3H,J=5.37 Hz), 0.80(d,3H,J=6.33 Hz).

EXAMPLE 15
Preparation of methyl A(1)-norursa-2-chloromethyl-23-chloro-2,12-diene-28-oate(13, $R_5$=Cl)

Excepting from substituting compound(12) for compound (8), the same procedure as example 8 was used (yield:12.8%).

IR(neat): 1719 $cm^{-1}$; $^1$H-NMR (400 MHz, $CDCl_3$): δ 5.61(s,1H), 5.27(t,1H), 4.21, 4.15(ABq,2H,J=9.8 Hz), 3.82, 3.72(ABq,2H,J=9.7 Hz), 3.63(s,3H), 2.22(d,1H), 1.23, 1.14, 1.06, 0.98, 0.84(each s,3H), 0.89(d,3H,J=6.4 Hz).

EXAMPLE 16
Preparation of methyl A(1)-norursa-2-methyl-2,12-diene-28-oate(14)

Excepting from substituting compound(13) for compound (9), the same procedure as example 10 was used (yield:27.0%).

IR(neat): 2925, 1726 $cm^{-1}$; Mass (EI): m/e 452($M^+$).

EXAMPLE 17
Preparation of methyl A(1)-norursa-2,12-diene-23-acetyloxy-2-formyl-28-oate(15)

Compound(5, 101.2 mg, 0.210 mmol) obtained above was dried under reduced pressure and replaced with argon. The resultant mixture was dissolved in anhydrous THF. Anhydrous acetic acid(39.6 μl) was added at room temperature and stirred for 2 hours. The solvent was removed under reduced pressure and the residue was diluted with ethyl acetate, washed and dried. The filtrate was concentrated under reduced pressure and refined separately with Column Chromatography(hexane:ethyl acetate=10:1) to obtain compound 94 mg (yield:85.5%).

IR(neat): 2927, 1686 $cm^{-1}$; Mass (EI): m/e 524($M^+$); $^1$H-NMR (400 MHz, $CDCl_3$): δ 9.71(s,1H), 6.61(s,1H), 5.28(t,1H,J=3.62 Hz), 4.03, 3.96(ABq,2H,J=10.92 Hz), 3.61 (s,3H), 2.24(d,1H), 2.06(s,3H), 1.24, 1.08, 1.05, 0.84(each s,3H), 0.93(d,3H,J=6.04 Hz), 0.84(d,3H,J=6.36 Hz).

EXAMPLE 18
Preparation of methyl A(1)-norursa-2-difluoromethyl-2,12-diene-23-acetyloxy-28-oate(16)

Excepting from substituting compound(15) for compound (12), the same procedure as example 13 was used (yield:38.8%).

IR(neat): 1239 cm$^{-1}$; Mass (EI): m/e 546(M$^+$); $^1$H-NMR (400 MHz, CDCl$_3$): δ 6.25(t,1H,J=55.4 Hz), 5.92(s,1H), 5.26(t,1H), 3.97, 3.86(ABq,2H,J=10.7 Hz), 3.61(s,3H), 2.24 (d,1H,J=9.92 Hz), 2.06(s,3H), 1.23, 1.11, 1.03, 0.95, 0.83 (each s,3H), 0.94(d,3H,J=6.12 Hz), 0.86(d,3H,J=6.4 Hz).

EXAMPLE 19
Preparation of methyl A(1)-norursa-2-hydroxymethyl-2,12-diene-23-acetyloxy-28-oate(17)

Excepting from substituting compound(15) for compound (7), the same procedure as example 6 was used (yield:78.2%).

IR(neat): 3503, 2926, 1718 cm$^{-1}$; Mass (EI): m/e 526 (M+); $^1$H-NMR(400 MHz, CDCl$_3$): δ 5.45(s,1H), 5.23(t, 1H,J=3.4 Hz), 4.29,4.20(ABq,2H,J=3.54 Hz), 3.92, 3.86 (ABq,2H,J=10.56 Hz), 3.61(s,3H), 2.21(d,1H), 2.04(s,3H), 1.17, 1.10, 1.00, 0.80(each s,3H), 0.94(d,3H,J=6.08 Hz), 0.85(d,3H,J=6.44 Hz).

EXAMPLE 20
Preparation of methyl A(1)-norursa-2-fluoromethyl-2,12-diene-23-acetyloxy-28-oate(18)

Excepting from substituting compound(17) for compound (12), the same procedure as example 13 was used (yield:27.9%).

IR(neat): 2927, 1740 cm$^{-1}$; Mass (EI): m/e 528(M$^+$), 529; $^1$H-NMR (500 MHz, CDCl$_3$): δ 5.49(s,1H), 5.17(t,1H,J=3.7 Hz), 4.94–4.79(m,2H), 3.87, 3.80(ABq,2H,J=10.7 Hz), 3.54 (s,3H), 2.17(d,1H), 1.99(s,3H), 1.19, 1.11, 1.04, 0.95, 0.75 (each s,3H), 0.87(d,3H,J=6.2 Hz), 0.79(d,3H,J=6.5 Hz).

EXAMPLE 21
Preparation of methyl A(1)-norursa-2-hydroxymethyl-12-ene-23-hydroxy-28-oate(19)

Compound(12, 15 mg, 0.031 mmol) obtained above was dissolved in ethanol and 10% Pd/C(3 mg) was added. The resultant was reacted for 5 hours with hydrogenator. Pd/C was filtrated, washed with methanol. The solvent was removed by evaporation under reduced pressure, and the residue was diluted with ethyl acetate, washed and dried. The filtrate was concentrated under reduced pressure and refined separately with column chromatography (hexane:ethyl acetate=15:1) to obtain compound 13.6 mg (yield:90%).

IR(neat):3468, 2927 cm$^{-1}$; Mass (EI): m/e 486(M$^+$); $^1$H-NMR (500 MHz, CDCl$_3$): δ 5.23(t,1H,J=4.53 Hz), 3.61 (s,3H), 3.32,3.26(d,2H,J=4.50 Hz), 2.21(d,2H), 1.10, 0.95, 0.89, 0.83, 0.75(each s,3H), 0.91(d,3H,J=8.25 Hz), 0.87(d, 3H, J=8.15 Hz).

EXAMPLE 22
Preparation of Compound(20)

Compound(5, 11 mg, 0.023 mmol) obtained above was dried under reduced pressure and replaced with argon. The resultant mixture was dissolved in anhydrous dichloromethane, and BF$_3$.OEt$_2$(0.28 µl) and 1,3-ethanedithiol(2.39 µl) were added sequentially. The resultant was concentrated under reduced pressure and refined separately with column chromatography(hexane:ethyl acetate=10:1) to obtain compound 7.8 mg (yield:61.3%).

IR(neat): 3448, 2926 cm$^{-1}$; $^1$H-NMR (300 MHz, CDCl3) δ 5.33(t,1H), 5.06(s,1H), 3.59(s,3H), 3.55, 3.37(ABq, 2H,J= 10.5 Hz), 3.29–3.15(m,4H), 2.64(bd, 1H), 2.47(d,1H,J=13.9 Hz), 1.09, 0.96, 0.69, (each s,3H), 0.85(d,3H,J=6.87 Hz).

EXAMPLE 23
Preparation of methyl A(1)-norursa-2-methyl-12-ene-23-hydroxy-28-oate(21)

Compound(20, 7.8 mg, 0.014 mmol) obtained above was dried under reduced pressure and replaced with argon. The resultant mixture was dissolved in anhydrous ethanol and and stirred for 4 hours with Raney Ni(0.47 ml) added. After filtration, the solvent was removed by evaporation under reduced pressure. The resultant was refined separately with column chromatography(hexane:ethyl acetate=10:1) to obtain compound 4.4 mg.(yield:66.97%)

IR(neat): 3471, 2927 cm$^{-1}$; $^1$H-NMR(300 MHz, CDCl$_3$): δ 5.33(t,1H), 3.59(s,3H), 3.45, 3.22(ABq, 2H,J=7.31 Hz), 2.27(d,1H,J=11.4 Hz), 1.16, 1.13, 1.08, 0.70, (each s,3H), 0.96(d,3H,J=3.66 Hz), 0.93(d,3H,J=5.37 Hz), 0.86(d,3H,J= 6.33 Hz).

EXAMPLE 24
Preparation of methyl A(1)-norursa-2-methyloxymethyl-2, 12-diene-23-O-t-butyldimethylsilyl-28-oate(22)

Compound(8, 15 mg, 0.025 mmol) obtained above was dried under reduced pressure, replaced with argon and dissolved in anhydrous THF. The resultant was added to sodium hydride(1.505 mg) washed with hexane and MeI (1.72 µl) was added after 1 hour. The resultant was heat-refluxed for 3 hours, was concentrated under reduced pressure, and refined separately with column chromatography(hexane:ethyl acetate=30:1) to obtain compound 10.9 mg.(yield:71%)

IR(neat): 2927,1725 cm$^{-1}$; Mass (EI): 612 m/e (M$^+$); $^1$H-NMR (400 MHz, CDCl$_3$) δ 5.38(s,1H), 5.22(t,1H), 3.98, 3.88(ABq,2HJ=6.83 Hz), 3.59(s,3H), 3.36, 3.28(ABq, 2H,J=9.28 Hz), 3.32(s,3H). 2.20(d,1H,J=10.3 Hz), 1.12, 1.08, 0.78, (each s,3H), 0.92(d, 3H, J=3.42 Hz), 0.83(d,3H, J=7.32 Hz), 0.85(s,9H), 0.00(s,6H).

EXAMPLE 25
Preparation of methyl A(1)-norursa-2-methyloxymethyl-2, 12-diene-23-hydroxy-28-oate(23)

Compound(22) obtained above was dried under reduced pressure and was dissolved in anhydrous THF. Tetrabutylammonium floride(5 µl) was added. The resultant was concentrated under reduced pressure, refined separately with column chromatography(hexane:ethyl acetate=10:1) to obtain compound 4 mg(yield:70.2%).

Mass (EI): 498 m/e (M$^+$); $^1$H-NMR (400 MHz, CDCl$_3$): δ 5.39(s,1H), 5.24(t,1H), 4.06, 3.92(ABq,2HJ=13.7 Hz), 3.61(s,3H), 3.45, 3.36(ABq, 2H,J=1026 Hz), 3.39(s,3H). 2.23(d,1H,J=11.7 Hz),1.17,1.12, 0.95, 0.81, (each s,3H), 0.90(d, 3H, J=7.32 Hz), 0.86(d,3H,J=6.35 Hz).

Experimental Example 1
Cytotoxicity of the Compounds

Cytotoxicity of the compounds was examined by using P388 lymphoid neoplasm cell line and MTT assay, a system which can examine cytotoxicity of components originated from natural products. As considering that clinical use asiatic acid derivatives, up to the present, is restricted to that on skin or the like, their cytotoxic effect was examined by using melanoma cell line (Malme-3M) and normal cell line (Detroit 551).

In case of a compound, up to 4 µg/ml of ED$_{50}$ value is recognized as being cytotoxic. The result was evaluated on this basis.

The Experimental method is described here-in-below:

Cells were cultured with various concentration of asiatic acid derivatives on microtitre plates in an incubator (37° C., 5% $CO_2$) for one day. 3-(4,5-Dimethylthiazol-2-yl)-2,5-diphenyl-tetrazolium bromine (MTT, Sigma, St. Louis, Mo., U.S.A.) solution was added thereto, and the amount of formazan thus formed was analyzed by a spectroscopic method. As a measure of cytotoxicity, $ED_{50}$ (concentration of a compound inhibiting 50% of cell growth) was used. As a control, $ED_{50}$ value of adriamycin was used.

TABLE 1

Cytotoxicity of asiatic acid derivatives having modified A-ring against various cell lines (P388D1, Malme-3M, Detroit551)

| Classification | P388D1 | Malme-3M | Detroit 551 |
|---|---|---|---|
| Compound 4 ($R_3$=H) | 6.81 | | |
| Compound 4 ($R_3$=methyl) | 4.3 ± 0.7 | 9.0 ± 0.8 | 27.8 ± 9.7 |
| Compound 5 ($R_3$=methyl) | 2.4 ± 0.7 | 2.9 ± 0.7 | 4.7 ± 0.9 |
| Compound 6 ($R_4$= -$C_2H_4CO_2H$) | 0.54 ± 0.21 | | |
| Compound 6 ($R_4$= -$COC_3H_6CO_2H$) | 4.06 ± 2.24 | | |
| Compound 6 ($R_4$= -$C_2H_2C_6H_5$) | 38.59 | | |
| Compound 6 ($R_4$=-$C_6H_5$) | 34.12 | | |
| Compound 11 ($R_3$=methyl) | 4.29 | | |
| Compound 12 ($R_3$=methyl) | 22.70 | | |
| ADR | 0.7 ± 0.1 | 1.0 ± 0.2 | |

TABLE 2

Effect of using asiatic acid derivatives having modified A-ring together with differentiation promotor, on P388D1

| | Single compound | With differentiation promotor | | | |
|---|---|---|---|---|---|
| | | HMBA (1 mM) | DMSO (1%) | NaB (3.75 mM) | LiCl (5 mM) |
| Compound4 ($R_3$=methyl) | 4.3 ± 0.7 | 2.0 ± 0.1 | 42.9 ± 3.4 | 2.5 ± 0.2 | 2.69 ± 0.4 |
| Compound5 ($R_3$=methyl) | 2.4 ± 0.7 | 2.0 ± 0.1 | 1.4 ± 0.4 | 0.6 ± 0.1 | 0.9 ± 0.4 |
| ADR | 0.7 ± 0.1 | 0.7 | 0.9 ± 0.1 | 0.1 | 0.1 |

P388D1: (ATCC CCL 46) Cell lines from rats of lymphoid neoplasm
MTT: Microculture tetrazolium assay was used. $ED_{50}$ (μg/ml, mean, +sd, n=3)
HMPA: hexamethylene bisacetamide
DMSO: dimethylene sulfoxide
NaB: Sodium boride
LiCl: Lithium chloride Experimental Example 2
Effect of Liver-protecting and Treatment of Asiatic Acid Derivatives on Liver Cell Toxicity Induced by Carbon tetrachloride or galactosamine The effect of liver-protecting and treatment of methyl A(1)-norursa-2-methyl-2,12-diene-23-hydroxy-28-oate, methyl A(1)-norursa-2,12-diene-23-succinyloxy-2-formyl-28-oate, methyl A(1)-norursa-2,12-diene-23-glutaryloxy-2-formyl-28-oate, methyl A(1)-norursa-2,12-diene-23-benzoyloxy-2-formyl-28-oate, methyl A(1)-norursa-2,12-diene-23-cinnamyloxy-2-formyl-28-oate and methyl A(1)-norursa-2-hydroxymethyl-2,12-diene-23-hydroxy-28-oate among the compounds (1) according to the present invention was examined.

For the experiment, male Wistars having 150–200 g of body weight were used. Before experiment, animals was fasted for one day, and the liver cells were isolated by using 2-step collagenase flow-out method [D. M. Crisp and C. I. Pogson, Biochem., 126, 1009 (1972)], of which the method is somewhat modified from that of Berry and Friend [M. N. Berry, D. S. Friend, J. Cell Biol., 43, 5006 (1969)].

Toxicity in liver cells by the use of carbon tetrachloride ($CCl_4$) was induced by culturing the isolated liver cells for 24 hours and then further culturing the same in a culture medium containing 10 mM carbon tetrachloride for 1.5 hours. [Y. Kiso, Y. Suzuki and H. Hikino, *Planta. Med.*, 49, 222(1983)]

On the other hand, toxicity of liver cells by galactosamine was induced by culturing the isolated liver cells for 1.5 hours, and then further culturing the same in a culture medium containing 1.5 mM galactosamine for 14 hours. [Y. Kris, M. Tohkin and H. Hikino, *J. Nat. Prod.*, 46, 841 (1983)]

The liver cells of which cytotoxicity have been induced was cultured in a culture medium containing the compound in a concentration of 5 μg/ml or 50 μg/ml. Then the cultured solution was taken to measure the activity of glutamic pyruvic transaminase (GPT) by means of Reitman-Frankel method. [S. Reitman and S. Frankel, *Am. J. Cli. Pathol.*, 28, 56 (1957)]

GPT value of normal liver cells without induction of toxicity was determined to 100%, and the value of toxilcity-induced liver cells without treatment with any compound was determined to 0%. Then the effect of recovery of liver toxicity by virtue of the compound was expressed as relative protection (%). The results are shown in Table 3.

TABLE 3

Liver-protecting effect of asiatic acid derivatives on toxicity-induced liver cells

| Compound | Liver cells having toxicity induced by $CCl_4$ | | Liver cells having toxicity induced by galactosamine | |
|---|---|---|---|---|
| | 5 μg/ml | 50 μg/ml | 5 μg/ml | 50 μg/ml |
| Methyl A(1)-norursa-2-methyl-2,12-diene-23-hydroxy-28-oate | 23 | 17 | 72 | 38 |
| Methyl A(1)-norursa-2,12-diene-23-succinyloxy-2-formyl-28-oate | — | — | 58 | 0 |
| Methyl A(1)-norursa-2,12-diene-23-glutaryloxy-2-formyl-28-oate, | 29 | 26 | 53 | 26 |
| Methyl A(1)-norursa-2,12-diene-23-benzoyloxy-2-formyl-28-oate, | — | — | 60 | 66 |
| Methyl A(1)-norursa-2,12-diene-23-cinnamyloxy-2-formyl-28-oate | 34 | 45 | 67 | 70 |
| Methyl A(1)-norursa-2-hydroxymethyl-2,12-diene-23-hydroxy-28-oate | 41 | 40 | 40 | 0 |

Methyl A(1)-norursa-2,12-diene-23-succinyloxy-2-formyl-28-oate, methyl A(1)-norursa-2-hydroxymethyl-2,12-diene-23-hydroxy-28-oate, the asiatic acid derivatives having modified A-ring of chemical formula (1) according to the present invention showed 23–41% of liver-protection in the liver cells having toxicity induced by 5 μg/ml carbon tetrachloride, while 40–72% of protection in the liver cells having toxicity induced by galactosamine.

FORMULATION EXAMPLES

| 1. Preparation of tablets (anti-cancer agent) | |
|---|---|
| active component | 2.5 mg |
| lactose BP | 151.0 mg |
| starch BP | 30.0 mg |
| pre-gelatinized corn starch BP | 15.0 mg |

The active component was sieved, and mixed with lactose, starch and pre-gelatinized corn starch. Suitable amount of purified water was added thereto and the mixture was granulated. After drying, the granules were mixed with magnesium stearate and pressed to prepare tablets.

| 2. Preparation of injection (anti-cancer agent) | |
|---|---|
| active component | 800 μg/ml |
| dilute hydrochloric acid BP | up to pH 3.5 |
| injectable sodium chloride BP | maximum 1 ml |

Active component was dissolved in proper amount of injectable sodium chloride BP, and the pH of the resultant solution was adjusted to 3.5 by adding dilute hydrochloric acid BP. Then the volume of the solution was adjusted by using injectable sodium chloride BP, and the solution was thoroughly mixed. The solution was charged in 5 ml type 1 ampoule made of transparent glass, and the ampoule was sealed under the upper lattice of air, by fusing the glass. Then the ampoule was sterilized by autoclaving at 120° C. for 15 minutes or more, to give injection.

| 3. Preparation of tablets (liver-protecting agent) | |
|---|---|
| methyl A(1)-norursa-2-methyl-2,12-diene-28-oate | 5.0 mg |
| lactose BP | 150.0 mg |
| starch BP | 30.0 mg |
| pre-gelatinized corn starch BP | 15.0 mg |
| magnesium stearate | 1.0 mg |

Methyl A(1)-norursa-2-methyl-2,12-diene-28-oate was sieved, and mixed with lactose, starch and pre-gelatinized corn starch. Suitable amount of purified water was added thereto and the mixture was granulated. After drying, the granules were mixed with magnesium stearate and pressed to prepare tablets.

| 4. Preparation of capsules (liver-protecting agent) | |
|---|---|
| methyl A(1)-norursa-2-methyl-2,12-diene-28-oate | 5.0 mg |
| starch 1500 | 100.0 mg |
| magnesium stearate BP | 1.0 mg |

Methyl A(1)-norursa-2-methyl-2,12-diene-28-oate was sieved and mixed with vehicles. The mixture was filled in gelatin capsules.

| 5. Preparation of injection (liver-protecting agent) | |
|---|---|
| methyl A(1)-norursa-2-hydroxymethyl-2,12-diene-23-hydroxy-28-oate | 1000 μg/ml |
| dilute hydrochloric acid BP | up to pH 3.5 |
| injectable sodium chloride BP | maximum 1 ml |

Methyl A(1)-norursa-2-hydroxymethyl-2,12-diene-23-hydroxy-28-oate was dissolved in proper amount of injectable sodium chloride BP, and the pH of the resultant solution was adjusted to 3.5 by adding dilute hydrochloric acid BP. Then the volume of the solution was adjusted by using injectable sodium chloride BP, and the solution was thoroughly mixed. The solution was charged in 5 ml type 1 ampoule made of transparent glass, and the ampoule was sealed under the upper lattice of air, by fusing the glass. Then the ampoule was sterilized by autoclaving at 120° C. for 15 minutes or more, to give injection.

As can be seen from the experimental examples, the asiatic acid derivatives according to the present invention showed excellent effect from the experiments of cytotoxicity against melanoma cells and of liver protecting effect on liver cells of which toxicity had been induced by carbon tetrachloride or galactosamine.

What is claimed is:

1. A compound, or a pharmaceutically acceptable salt or ester thereof, represented by formula 1

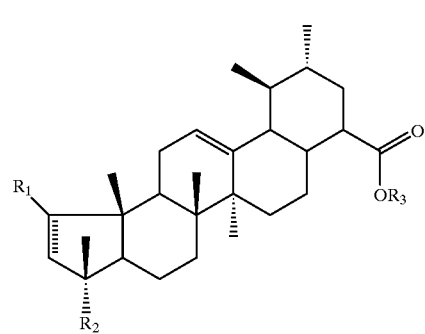

wherein:
  $R_1$ is chosen from a lower alkyl group having 1–4 carbon atoms, an alkoxy group having 1–4 carbon atoms, a hydroxymethyl group, a halomethyl group, an aldehyde group, and an aldehyde group protected by ethanedithiol;
  $R_2$ is chosen from a lower alkyl group having 1–4 carbon atoms, a halomethyl group, a t-butyldimethylsilyloxymethyl group, a hydroxymethyl group, a hydroxymethyl group protected by an acetyl or benzoyl group, —$CH_2OCOCHCHC_6H_5$ and —$CH_2OCO(CH_2)_nCO_2H$, wherein n is chosen from 0, 1, 2 and 3;
  $R_3$ is chosen from —H and —$CH_3$; and
  wherein the double bond at the 2-position may be reduced,
with the proviso that when $R_1$ is —CHO and $R_2$ is hydroxymethyl $R_3$ is not —$CH_3$.

2. A pharmaceutical composition comprising a compound, or a pharmaceutically acceptable salt or ester thereof, represented by formula 1

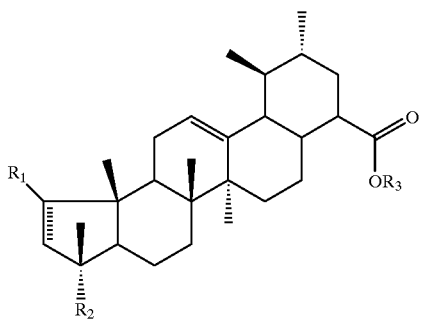

wherein:
R₁ is chosen from a lower alkyl group having 1–4 carbon atoms, an alkoxy group having 1–4 carbon atoms, a hydroxymethyl group, a halomethyl group, an aldehyde group, and an aldehyde group protected by ethanedithiol;
R₂ is chosen from a lower alkyl group having 1–4 carbon atoms, a halomethyl group, a t-butyidimethylsilyloxymethyl group, a hydroxymethyl group, a hydroxymethyl group protected by an acetyl or benzoyl group, —CH₂OCOCHCHC₆H₅ and —CH₂OCO(CH₂)ₙCO₂H, wherein n is chosen from 0, 1, 2 and 3;
R₃ is chosen from —H and —CH₃; and
wherein the double bond at the 2-position may be reduced,
and a pharmaceutically acceptable carrier.

3. A method of treating cancer comprising administering to a patient in need of such treatment, a therapeutically effective amount of a compound, or a pharmaceutically acceptable salt or ester thereof, represented by formula 1

1

[structure similar to above]

wherein:
R₁ is chosen from a lower alkyl group having 1–4 carbon atoms, an alkoxy group having 1–4 carbon atoms, a hydroxymethyl group, a halomethyl group, an aldehyde group, and an aldehyde group protected by ethanedithiol;
R₂ is chosen from a lower alkyl group having 1–4 carbon atoms, a halomethyl group, a t-butyidimethylsilyloxymethyl group, a hydroxymethyl group, a hydroxymethyl group protected by an acetyl or benzoyl group, —CH₂OCOCHCHC₆H₅ and —CH₂OCO(CH₂)ₙCO₂H, wherein n is chosen from 0, 1, 2 and 3;
R₃ is chosen from —H and —CH₃; and
wherein the double bond at the 2-position may be reduced.

4. A method of treating hepatotoxicity comprising administering to a patient in need of such treatment, a therapeutically effective amount of a compound, or a pharmaceutically acceptable salt or ester thereof, represented by formula 1

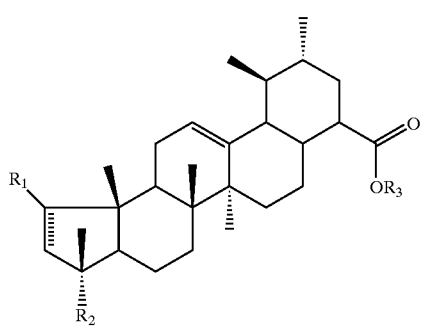

wherein:
R₁ is chosen from a lower alkyl group having 1–4 carbon atoms, an alkoxy group having 1–4 carbon atoms, a hydroxymethyl group, a halomethyl group, an aldehyde group, and an aldehyde group protected by ethanedithiol;
R₂ is chosen from a lower alkyl group having 1–4 carbon atoms, a halomethyl group, a t-butyldimethylsilyloxymethyl group, a hydroxymethyl group, a hydroxymethyl group protected by an acetyl or benzoyl group, —CH₂OCOCHCHC₆H₅ and —CH₂OCO(CH₂)ₙCO₂H, wherein n is chosen from 0, 1, 2 and 3;
R₃ is chosen from —H and —CH₃; and
wherein the double bond at the 2-position may be reduced.

* * * * *